United States Patent [19]
Thompson

[11] Patent Number: 6,004,260
[45] Date of Patent: Dec. 21, 1999

[54] INTRAUTERINE DELIVERY ARRANGEMENT

[75] Inventor: Ronald J Thompson, Ft. Thomas, Ky.

[73] Assignee: Medworks Corp, Louisville, Ky.

[21] Appl. No.: 09/023,265

[22] Filed: Feb. 13, 1998

Related U.S. Application Data

[63] Continuation-in-part of application No. 08/953,063, Oct. 17, 1997.
[51] Int. Cl.$^6$ ..................................................... A61B 17/43
[52] U.S. Cl. .............................................................. 600/33
[58] Field of Search ........................... 600/33–35; 604/19, 604/27, 28, 30–34, 36, 38, 54, 55, 73, 96

[56] References Cited

U.S. PATENT DOCUMENTS

| 3,811,443 | 5/1974 | Dickinson, III et al. | ................. 600/35 |
|---|---|---|---|
| 5,084,004 | 1/1992 | Ranoux | ..................................... 600/34 |
| 5,536,243 | 7/1996 | Jeyendran | ................................. 600/35 |

*Primary Examiner*—Samuel Gilbert
*Attorney, Agent, or Firm*—Don Halgren

[57] ABSTRACT

The present invention comprises an apparatus and method for the application of a treatment medium to the intrauterine cavity of a female. The method includes the steps of introducing a first pressurizable chamber within a intrauterine cavity of a female; introducing a second pressurizable chamber readily outwardly of the first pressurizable chamber; filling the first pressurizable chamber with a treatment medium; and filling the outer pressurizable chamber with a pressurizable fluid, so as to affect discharge of the treatment medium from the innermost first pressurizable chamber over an extended period of time. The method includes the step of introducing the treatment medium into the first pressurizable chamber through an elongated catheter. The treatment medium may be comprised of a medicament or of spermatozoa for insemination of the female.

21 Claims, 11 Drawing Sheets

INTRAUTERINE DELIVERY ARRANGEMENT

Application is a Continuation-In-Part of my earlier co-pending U.S. patent application Ser. No. 08/953,063, filed Oct. 17, 1997 pending, and incorporated herein by reference, in its entirety.

BACKGROUND OF THE INVENTION

1. Field of the Invention

This invention relates to dispensing instruments and methods for introducing treatment material and fluid-like material into the uterus and canals of the fallopian tubes, and more particularly to a method in apparatus for the effecting of insemination. This

2. Prior Art

Specific delivery and application of a treatment medium such as spermatozoa, to an intrauterine locus, particularly for the successful insemination of an egg thereat, is an intended yet illusive goal of many in the medical field. Successful fertilization requires the maturation of spermatozoa in their transit through the uterus and oviducts to the ovum. The goal of the fertilization process, is to promote changes in the female reproductive tract and increase the ability of sperm to penetrate the egg, this effect being called capacitation.

The likelihood of such fertilization occurs, by the successful delivery of the spermatozoa and its association with the extracellular coating of the oval called the zone pellucid. Once a successful motile spermatozoon has fused with the egg membrane, fertilization has been completed. For this to occur, however, millions of spermatozoa must be successfully released so that one of them reaches the egg at the optimum time. This time window for such spermatozoa within the uterus, from introduction to fertilization, may extend in range over a twenty-four to a sixty hour period.

One approach for delivering material into the female uterus is shown in U.S. Pat. No. 4,182,328 to Bolduc et al. This patent shows a dispensing instrument utilizing a balloon which is inflated within the uterus. A piston and cylinder arrangement has a duct that extends through the balloon, which feeds the material to the uterus. The material is delivered over a short period of time and the balloon and probe are readily withdrawn thereafter. A further concept to Bolduc, is shown in U.S. Pat. No. 4,547,188 with a complicated housing and injector assembly with a conduit path through a balloon for treatment of a female uterus.

U.S. Pat. No. 4,654,025 to Cassou et al, discloses an insemination apparatus for animals, utilizing a flexible injector probe, having a plurality of expandable balloons one of each end thereof to facilitate injection of semen from a reservoir tube into the vaginal cavity of the animal. U.S. Pat. No. 5,104,377 to Levine et al, shows a device for accessing and introducing fluids into the female uterus. This device uses several spaced-apart balloons to securely couple the shaft to the uterus, adjusting to the length of the cervical canal. U.S. Pat. No. 5,372,584 to Zink et al, shows an apparatus for establishing access to the uterus and fallopian tubes of a female. An anchoring tube on the end of a flexible catheter is first inserted within the uterus. After such anchoring is completed, the elongated second catheter is arranged to extend through the first catheter and balloon and into the fallopian tubes. Injection of treatment into those fallopian tubes is thereby accomplished.

U.S. Pat. No. 5,562,654 to Smith et al, shows an arrangement for time-released delivery of a preparation into a uterine cavity. An osmotic pump is placed within the vagina of the female, having a delivery tube extending within the uterus. An anchoring balloon is disposed about the delivery tube within the uterus and is pressurized through a port which is pressurized through the vagina. Osmotic pressure gradually builds up within the osmotic chamber to pressurize an inner chamber to deliver material from the vagina to within the uterus through the delivery tube.

It is an object of the present invention, to overcome the limitations and objections of the prior art.

It is a further object of the present invention, to provide a unique method and apparatus for treatment of a mammalian uterus, in a safe and comfortable manner over an extended period of time, for optimization of the intended results.

It is still yet a further object of the present invention, to provide a method and apparatus for the fertilization of a human or animal female wherein unnecessary medical procedures are eliminated.

BRIEF SUMMARY OF THE INVENTION

The present invention is an apparatus and method to permit millions of spermatozoa to spend some hours in the female tract in order to maximize its capacity to penetrate the ovum. This sperm capacitation is facilitated in the present invention by an insertable introduction apparatus intended for relatively long-term emplacement.

The insertion apparatus comprises of an elongated flexible hollow catheter shaft. The hollow catheter shaft has a proximal end that is in fluid communication with a syringe and a displaceable inserting stem. This stem acts as a plunger. The syringe housing is pre-loaded with a treatment media therein, the treatment media comprising for example, sperm or medicaments. The hollow elongated catheter shaft has a distal end including a discharge orifice, which orifice is in fluid communication with the lumen within the catheter shaft. The discharge orifice extends out the side walls of the catheter shaft. The distalmost end of the catheter shaft is rounded, so as to provide a blunt end. A flexible radially expandable reservoir chamber or balloon is disposed about the distal end of the catheter shaft. The reservoir balloon has a proximal end which is in engagement with an annular seal which is a sliding sealing arrangement with the distal end of the hollow catheter shaft.

A step, or annual ring, is arranged at a location for example, about several centimeters from the distalmost end of the catheter shaft. The step or annual ring limits the proximal motion of the annular seal on the proximal end of the reservoir balloon. The reservoir balloon has a distal end which is in annular engagement with a distalmost release valve. The distalmost release valve may for example, be a duck bill or a flat slit valve which permits slow discharge of treatment medium from within the reservoir when the reservoir is under pressure. A second chamber, such as for example, an outer, flexible, radially expanding retention balloon, is arranged radially outwardly of the reservoir balloon about the distal end of the hollow catheter shaft. The outer retention balloon has a distalmost end which is in sealing engagement with the distalmost end of the first chamber and/or annular release valve at the distal end of the inner reservoir balloon. The outer retention balloon has an elongated neck extending proximately therefrom and also about the catheter shaft, and has an end seal on its proximalmost portion of that elongated neck of the retention balloon. The end seal is in close fitting relation about the hollow catheter shaft. The elongated neck on the retention balloon is configured so as to extend between the uterus and the cervix, through the endocervical canal of the female reproduction system.

The end seal on the proximalmost end of the neck of the retention balloon comprises a displaceable and dislodgeable valve, which is removable from the neck of the retention balloon, by a pull-string, which string extends proximately therefrom.

In operation of the present insertion apparatus, the syringe on the proximalmost end of the elongated hollow catheter shaft is preferrably pre-loaded with a several cc charge of treatment medium, such as a medicament or a charge of spermatozoa. The elongated hollow catheter shaft with its empty deflated inner reservoir balloon and its empty deflated retention balloon therearound, are pushed through the vagina, through the endocervical canal, and then into the female intrauterine cavity. After the innermost reservoir balloon, the outer retention balloon, and the distalmost end of the elongated hollow catheter shaft have entered the intrauterine cavity, the syringe is actuated, to push a charge of treatment media or sperm therethrough, and into the reservoir balloon, filling that reservoir balloon with one to two cc's of treatment medium or spermatozoa. During entry of the reservoir into the intrauterine cavity, the step arrangement on the outside of the catheter shaft, near the distal end thereof, pushes the annular seal of the proximal end of the reservoir and the chambers on the distal end of the catheter shaft into its forwardmost distally directed motion, and also ensuring that the reservoir balloon does not slide down proximately, on the hollow catheter shaft.

Upon the filling of a treatment medium or sperm solution from the syringe into the reservoir balloon, the hollow catheter shaft is withdrawn proximally from fluid communication with the reservoir balloon. The discharge orifice adjacent the distal end of the hollow catheter shaft is then next in fluid communication with the inside volume of the second chamber or outer retention balloon. The syringe holding the pre-load of treatment medium or sperm is removed, and a clean syringe is utilized for injection of about 2 cc of air through that same lumen of the catheter shaft, and out the discharge orifice and into the outer retention balloon within the uterine cavity. The retention balloon is thereby inflated to a predetermined pressure or volume of fluid such as for example, air. The end seal at the proximal location on the elongated neck of the retention balloon prevents air from escaping between the elongated catheter shaft and the retention balloon, the elongated neck extending through the endocervical canal. The annular ring valve at the distal end of the retention balloon is sealingly arranged thereat, so as to prevent fluid/air from escaping the retention balloon and into the uterus. The annular seal at the proximal end of the reservoir balloon is automatically self-sealed upon retractive removal of the distalmost end of the elongated hollow catheter shaft therefrom.

Thus in the initial time-release phase of the operation of the present invention, the retention balloon is inflated within the intrauterine cavity and provides a radially inwardly directed pressure upon the reservoir balloon therewithin, which reservoir balloon already having been injectably filled with the pressurized treatment medium or sperm. The elongated neck extending proximately from the retention balloon is still arranged through the endocervical canal. As the female containing using this device moves or as the user's uterus contracts because of pressure on the lower uterine segment, a corresponding pressure on the retention balloon causes a corresponding expelling pressure on the reservoir balloon, so as to initiate a slow release discharge-treatment of media or sperm, over an extended period of time, through the release valve at the distalmost end of the reservoir balloon and into the uterine cavity.

The retention balloon and the reservoir balloon are maintained within the intrauterine cavity over an extended period of time, for example, about 24 to 60 hours. During the first twenty-four hours of emplacement of the insertion apparatus within the intrauterine cavity, a continuous supply of treatment medium or capacitated sperm is supplied through the release valve and into the uterus and fallopian tubes. During the next twenty-four hours of emplacement of the insertion apparatus within the intrauterine cavity, the reservoir balloon becomes substantially deflated, and has discharged its volume of treatment medium or spermatozoa. This total elapsed time of about forty-eight hours is sufficient to provide a medicament treatment or a continuum of capacitated sperm to the fallopian tubes and ovum, to ensure fertilization in a most nearly natural manner. Diminishment of volume of the reservoir balloon is accompanied by a corresponding volumetric diminishment of the outer retention balloon.

After about sixty hours post-insertion of the insertion apparatus, the draw or pull-string attached to the proximal-most end of the elongated neck on the retention neck, may be pulled so as to release the escape valve thereat. The outer retention balloon is thereby deflated, and the entire remaining reservoir balloon and retention balloon may be easily and safely removed from the intrauterine cavity through the endocervical canal, and may be discarded. This procedure permits removal of this device without necessitating a return visit to a physician's office.

Thus, intrauterine treatment of a female, human or animal, may be accomplished for insemination or treatment by a medicament, through a process which closely corresponds to a natural insemination, for an extended period of time such being the most likely to cause proper fertilization. The invention thus comprises a method and an apparatus to permit the supply of a medicament or a capacitated spermatozoa to the fallopian tube for a forty eight to sixty hour continuous window, with only one introduction/insemination thereof. The invention also comprises a method and an apparatus shown which minimizes the exposure of spermatozoa. The invention also comprises a method and apparatus to obstruct the lower uterine segment and the endocervix to prevent the cervical loss of treatment medium or sperm during transcervical intrauterine introduction/insemination, which would otherwise be caused by a strong uterine contraction in response to the foreign antigenic substance (the spermatozoa). The invention also comprises a method and apparatus for the placement of one to two cc's of a concentrated treatment medium or a spermatozoa preparation into the intrauterine cavity during a single introduction/insemination. The invention also comprises a method and apparatus which utilizes the natural uterine contractions stimulated by the pressure of the retention balloon creating pressure in the lower uterine segment of the uterus, thus acting as a pump, to expel medicament and/or spermatozoa from the treatment/medium/sperm reservoir into the intrauterine cavity/fallopian tube environment. The invention also comprises a method and apparatus to place one to two cc's of a concentrated treatment medium or spermatozoa, during a single introduction process or insemination (current IUI procedure recommends only 0.3 to 0.5 cc's of spermatozoa preparation to be placed in the uterus because of the exaggerated antigen reaction of the uterus—contractions which would expel the specimen transcervically). The invention also comprises an apparatus and method to present spermatozoa to the intrauterine cavity without an injecting force as needed in current intrauterine insemination, (the injection force by the physician on the syringe attached to the IUI tube can expel an oocyte already in the tubal ampula, out in a retrograde manner and into the peritoneal cavity. The invention also comprises a method and apparatus to allow a patient to remove the treatment/ insemination device without the necessity of further visits to a physician's office.

BRIEF DESCRIPTION OF THE DRAWINGS

The objects of the present invention will become more apparent, when viewed in conjunction with following drawings, in which:

FIG. 2 A is a side elevational view of an insertion apparatus constructed according to the principals of the present invention;

DESCRIPTION OF THE PREFERRED EMBODIMENTS

Figure 1:
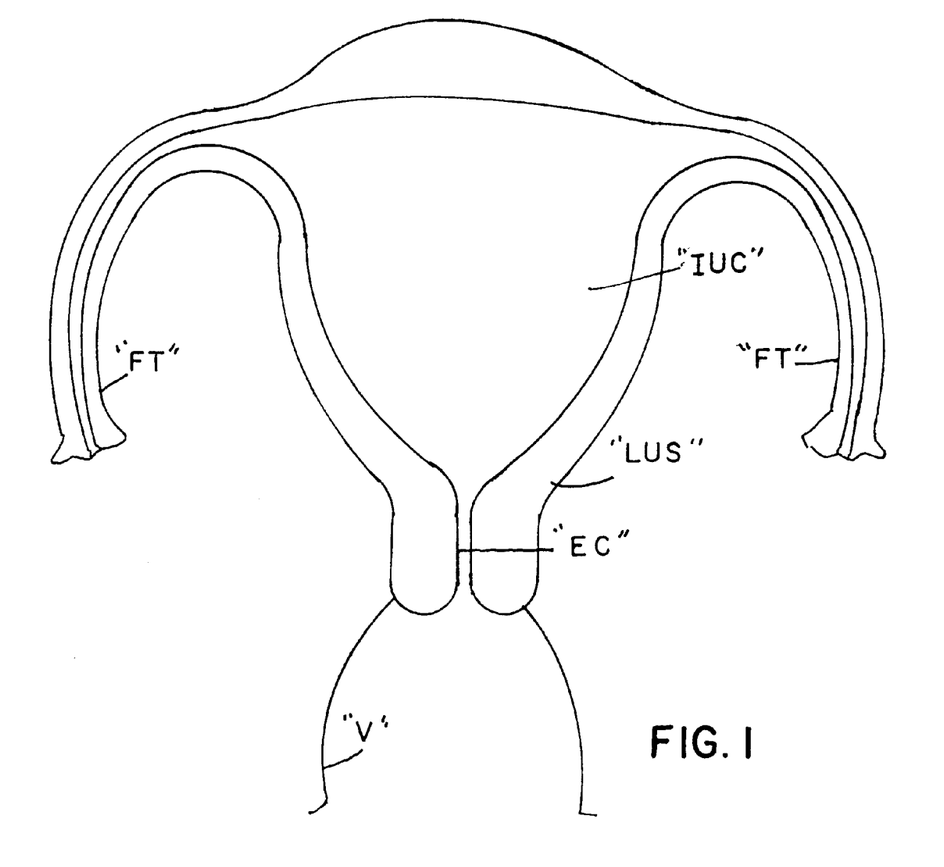
FIG. 1 is an anatomical representation of the female reproductive system.

The present invention is an apparatus and method for the treatment of a female reproductive tract, as represented in FIG. 1, and to permit millions of spermatozoa to spend some hours in the female reproductive tract in order to maximize its capacity to penetrate the ovum. This sperm capacitation is facilitated in the present invention by an insertable introduction apparatus 20, shown in FIGS. 2 and 2A, and intended for relatively long-term emplacement (i.e. about 24 to about 60 hours).

Figure 2:
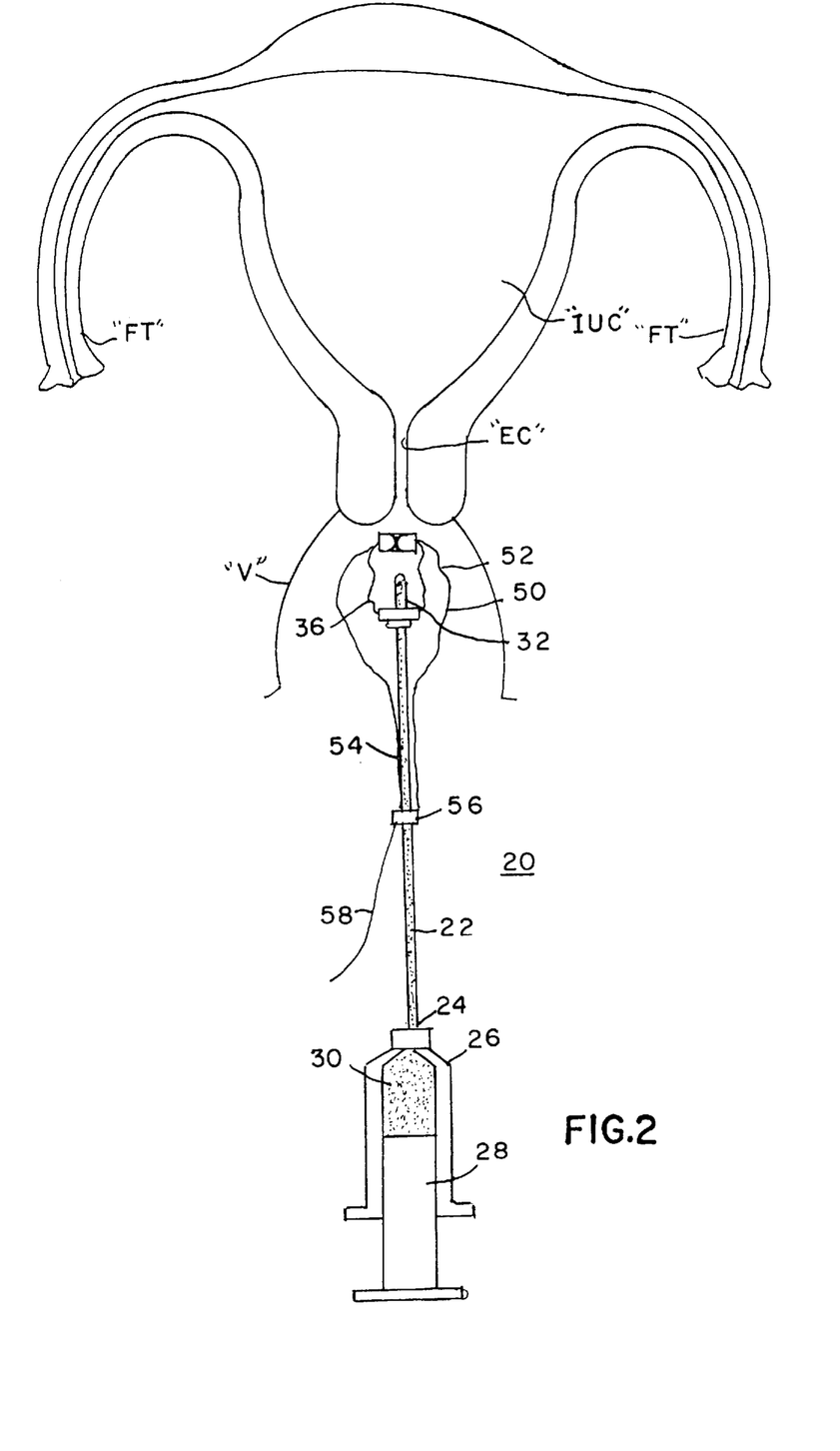
FIG. 2 is a representation of the insertion apparatus transcervically, initially into the vagina.
Figure 2A:
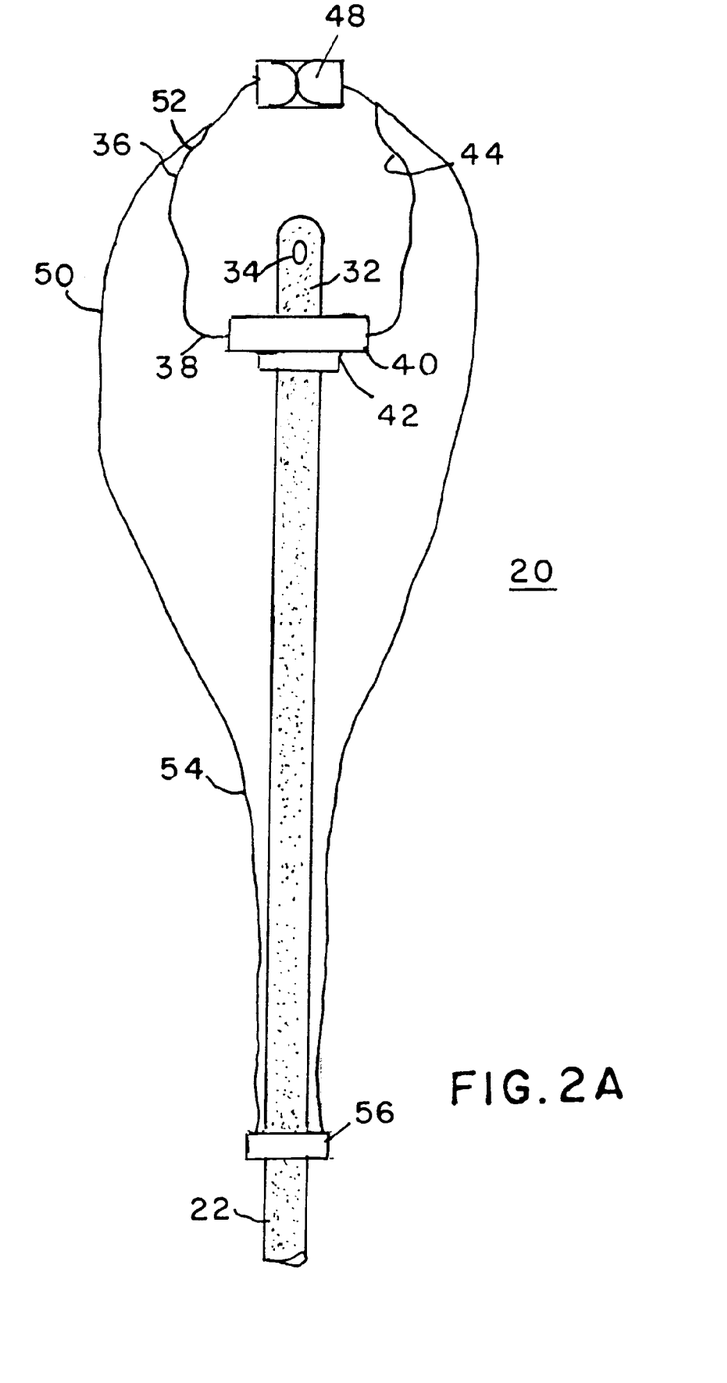

The insertion apparatus 20 comprises of an elongated flexible hollow catheter shaft 22. The hollow catheter shaft 22 has a proximal end 24 that is in fluid communication with a syringe 26 and a displaceable inserting stem 28. This stem 28 acts as a plunger. The syringe 26 housing is pre-loaded with a treatment media 30 therein, for example, sperm or medicaments. The hollow elongated catheter shaft 22 has a distal end 32 including a discharge orifice 34 which is in fluid communication with the lumen within the catheter shaft 22. The discharge orifice 34 extends out the side walls of the catheter shaft 22. The distalmost end of the catheter shaft 22 is rounded, so as to provide a blunt end. A first chamber or flexible radially expandable reservoir balloon 36 is disposed about the distal end 32 of the catheter shaft 22. The reservoir balloon 36 has a proximal end 38 which is in engagement with an annular seal 40 which is a sliding sealing arrangement with the hollow catheter shaft 22.

A step, or annual ring 42, is arranged at a location of about several centimeters from the distalmost end of the catheter shaft 22. The step or annual ring 42 limits the proximal motion of the annular ring or seal 42 on the proximal end 38 of the reservoir balloon 36. The reservoir balloon 36 has a distal end 44 which is in annular engagement with a distalmost release valve 48. The distalmost release valve 48 may for example, be a duck bill or a flat slit valve which permits slow discharge of medium 30 from within the reservoir 36 when the reservoir 36 is under pressure. A second chamber 50 for example, an outer, flexible, radially expanding retention balloon is arranged radially outwardly of the reservoir balloon 36 about the distal end 32 of the hollow catheter shaft 22. The outer retention balloon 50 has a distalmost end 52 which is also in sealing engagement with the annular release valve 48 at the distal end 44 of the inner reservoir balloon 36. The outer retention balloon 50 has an elongated neck 54 which extends proximately about the catheter shaft 22, and has an end seal 56 on its proximalmost portion of the elongated neck 54 of the retention balloon 36, as may be seen in FIGS. 2 and 2A. The end seal 56 is in close fitting relation about the hollow catheter shaft 22. The elongated neck 54 on the retention balloon 50 is configured so as to extend between the uterus and the cervix, through the endocervical canal "EC" of the female reproduction system, as may be seen in FIG. 3 et seq.

The end seal 56 on the proximalmost end of the neck 54 of the retention balloon 50 comprises a displaceable and dislodgeable valve which is removable from the neck 54 of the retention balloon 50 by a pull-string 58, which string 58 extends proximately therefrom, as may be seen in FIG. 2 et seq.

Figure 3:
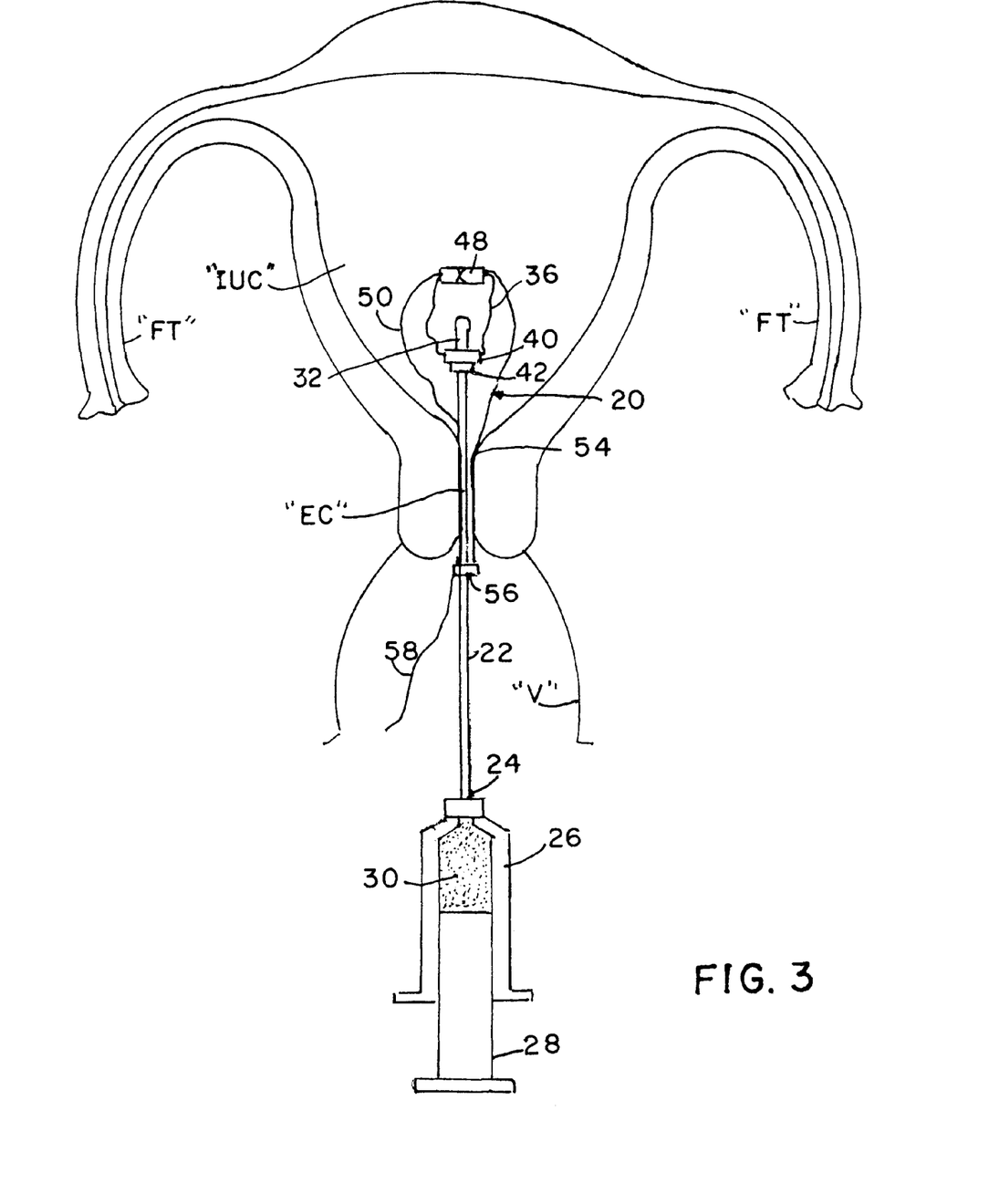
FIG. 3 is a representation of the placement of the insertion apparatus within the intrauterine cavity, showing the syringe and treatment containing syringe at the proximalmost end thereof.
Figure 4:
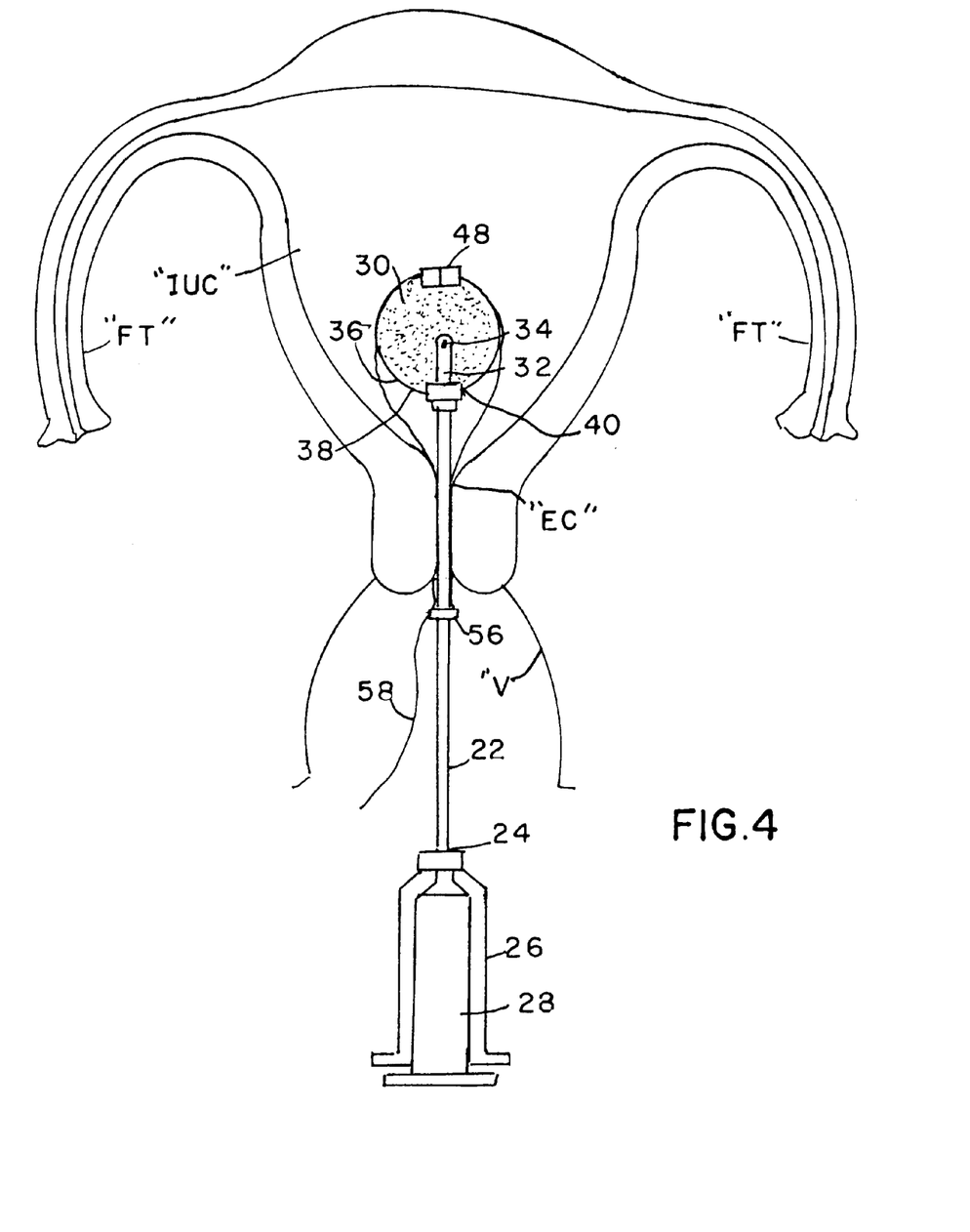
FIG. 4 is a representation of the uterine cavity with the reservoir balloon of the insertion apparatus being filled.

In operation of the present insertion apparatus 20, the syringe 26 on the proximalmost end of the elongated hollow catheter shaft is pre-loaded with a several cc charge of treatment medium, such as a medicament or a charge of spermatozoa. The elongated hollow catheter shaft 22 with its empty deflated inner reservoir balloon 36 and its empty deflated retention balloon 50 therearound, are pushed through the vagina "V", as represented in FIG. 2, then through the endocervical canal "EC", and then into the female intrauterine cavity "IUC", as represented in FIG. 3. After the innermost reservoir balloon 36, the outer retention balloon 50, and the distalmost end 32 of the elongated hollow catheter shaft 22 have entered the intrauterine cavity "IUC", the syringe 26 is actuated, to push a charge of treatment or sperm 30 therethrough, and into the reservoir balloon 36, pressurizably filling that reservoir balloon 36 with one to two cc's of treatment medium or spermatozoa 30, as represented in FIG. 4. During entry of the reservoir balloon 36 into the intrauterine cavity "IUC", the step arrangement 42 adjacent on the outside of the catheter shaft 22 near the distal end of that hollow catheter shaft 22, causes the annular seal 40 and the inner and outer chambers 36 and 50 in forwardmost distally-directed motion, thus ensuring that the reservoir balloon 36 does not slide down proximately on the hollow catheter shaft 22.

Figure 5:
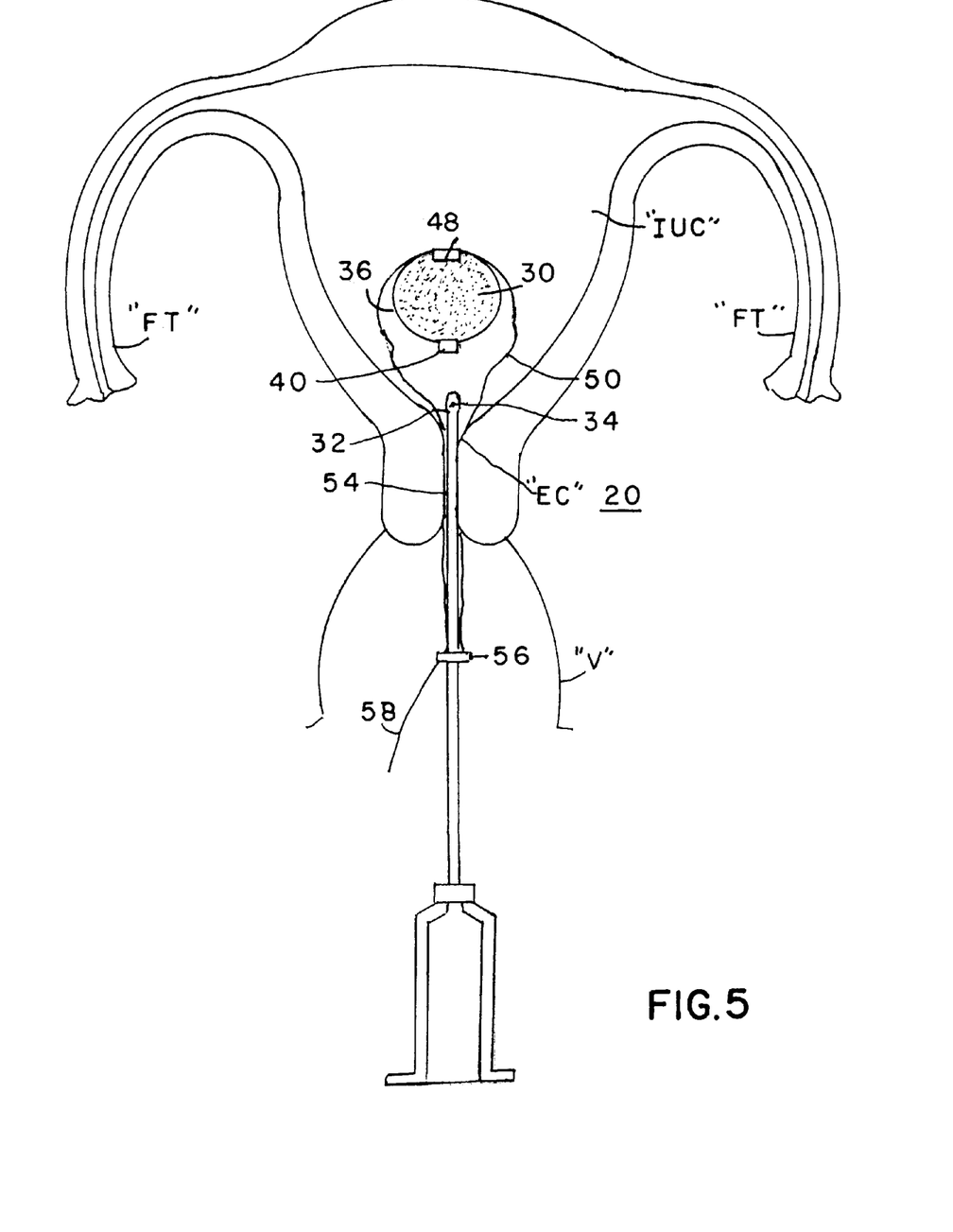
FIG. 5 is a representation of the uterine cavity with the reservoir balloon being filled and the catheter shaft of the insertion apparatus being displaced, so as to permit the filling of the retention balloon.
Figure 6:
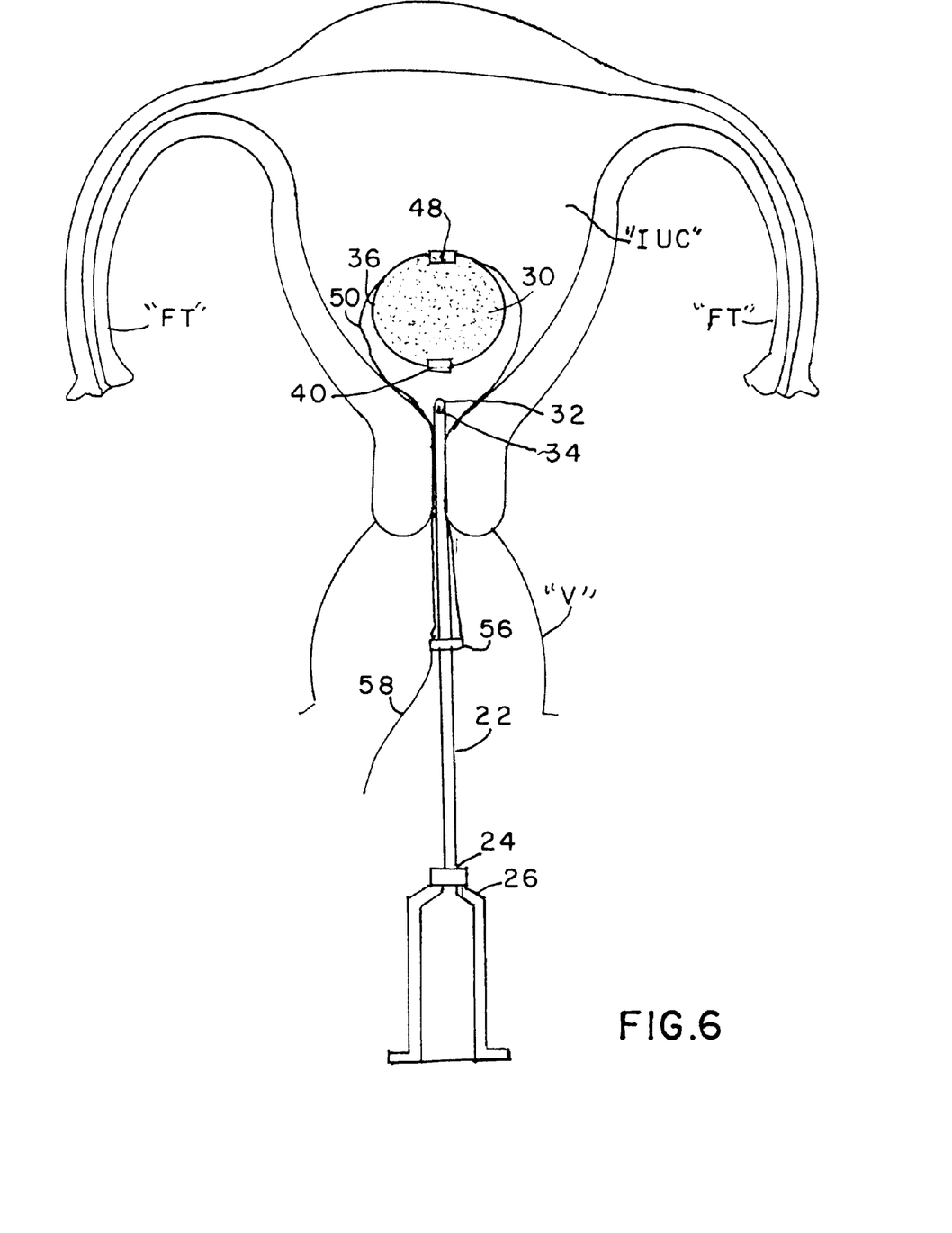
FIG. 6 is a representation of the intrauterine cavity with the retention balloon being filled by the catheter shaft and syringe thereattached.

Upon the filling of a treatment medium or sperm solution 30 from the syringe 26 into the reservoir balloon 36, the hollow catheter shaft 22 is withdrawn from fluid communication with the reservoir balloon 36, as is represented in FIG. 5. The discharge orifice 34 adjacent the distal end 32 of the hollow catheter shaft 22 is then next in fluid communication with the inside volume of the second chamber or outer retention balloon 50. The syringe 26 holding the pre-load of treatment medium or sperm 30 is removed, and a clean syringe, for injection of about 2 cc of air through that same lumen of the catheter shaft, and out the discharge orifice and into the outer retention balloon within the uterine cavity. The retention balloon is thereby inflated to a predetermined pressure or volume of air, as represented in FIG. 6. The end seal 56 at the proximal location on the elongated neck 54 of the retention balloon prevents air from escaping between the elongated catheter shaft 22 and the retention balloon 50. The annular ring valve 48 at the distal end 52 of the retention balloon 50, is sealingly attached thereto, so as to prevent air from escaping the retention balloon 50 and into the uterus "IUC". The annular seal 56 at the proximal end of the reservoir balloon 50 is automatically self-sealed upon removal of the distalmost end 32 of the elongated hollow catheter shaft 32 therefrom, as represented in FIG. 7.

Figure 7:
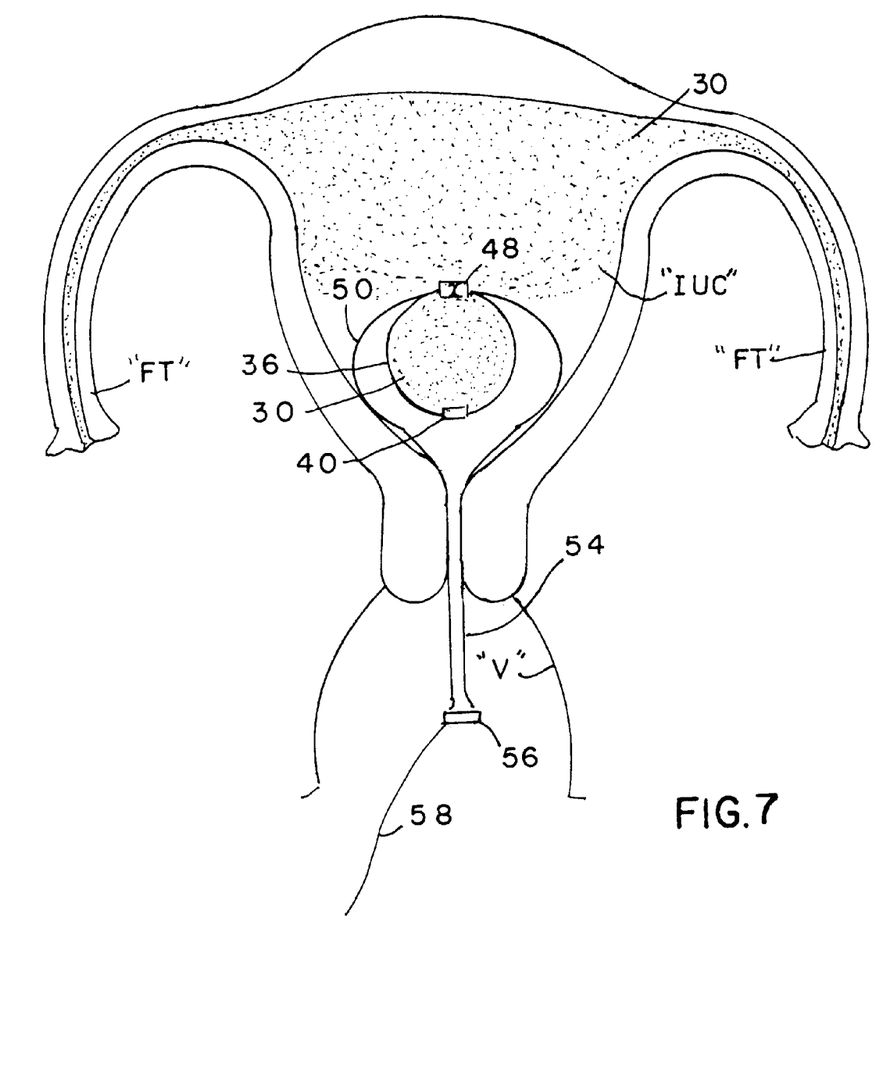
FIG. 7 is a representation of the intrauterine cavity with the reservoir balloon and the retention balloon in place, at the initial stages of the proposed treatment.

Thus in the initial time-release phase of this operation, after the retention balloon 50 is inflated within the intrauterine cavity, as represented in FIG. 7, the retention balloon 50 provides a radially inwardly directed pressure upon the reservoir balloon 36 therewithin, which the reservoir balloon 36 contains the treatment medium or sperm 30. The elongated neck 54 extending proximately from the retention balloon 50 is still arranged through the endocervical canal "EC". As the female moves or as the uterus "IUC" contracts because of pressure on the lower uterine segment, a corresponding pressure on the retention balloon 50 causes a corresponding expelling pressure on the reservoir balloon 36, so as to discharge treatment media or sperm 30, over an extended period of time, through the valve 48 at the distalmost end 52 of the reservoir balloon 50 and into the uterine cavity "IUC".

Figure 8:
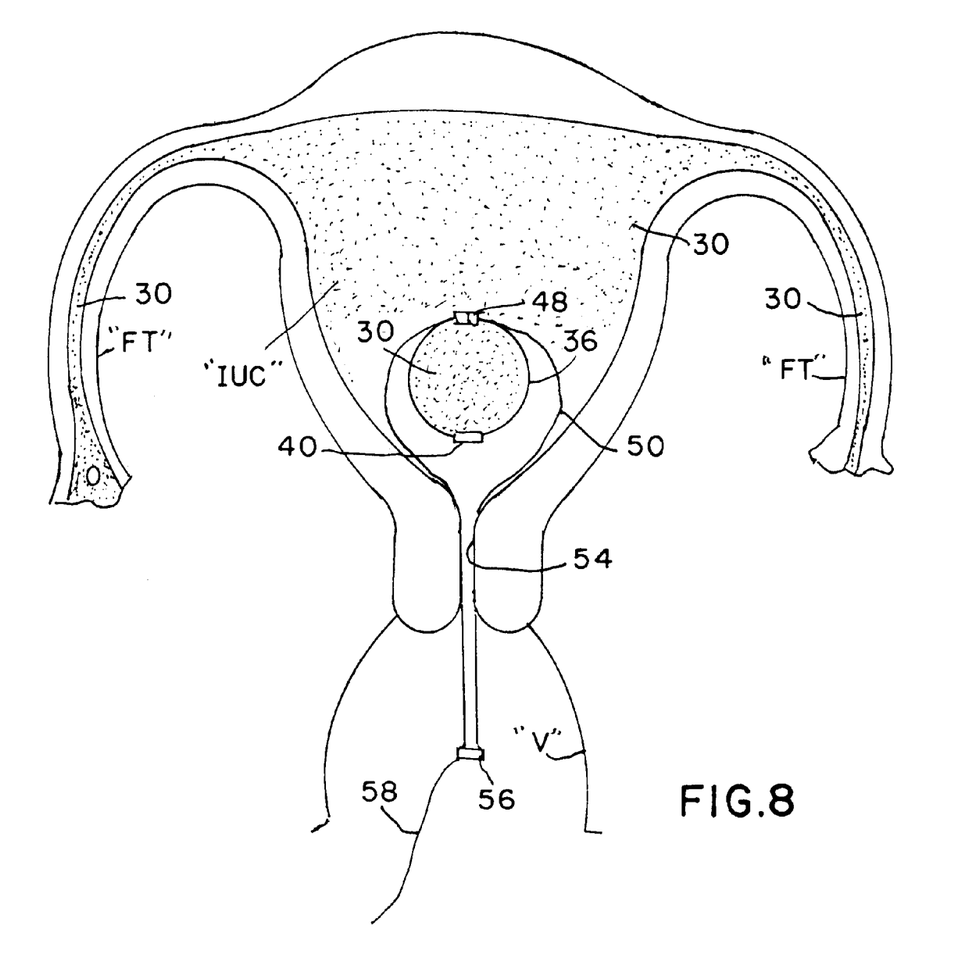
FIG. 8 is a representation of the uterine cavity at a time-lapse of about twenty-four hours in the treatment process, with the reservoir balloon and retention balloon therewithin.
Figure 9:
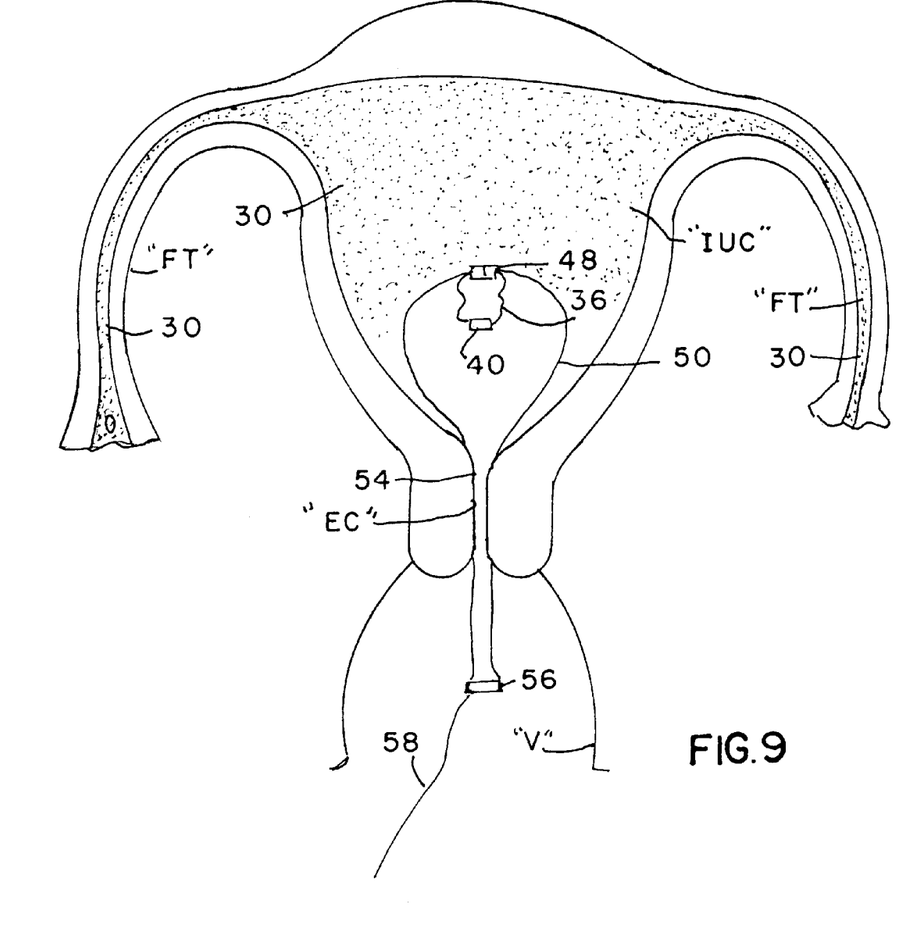
FIG. 9 is a representation of the uterine cavity after a time-lapse of about forty-eight hours into the treatment process, showing the reservoir balloon and the retention balloon therewithin, and the treatment medium dispersed within the uterus and the fallopian tubes.
Figure 10:
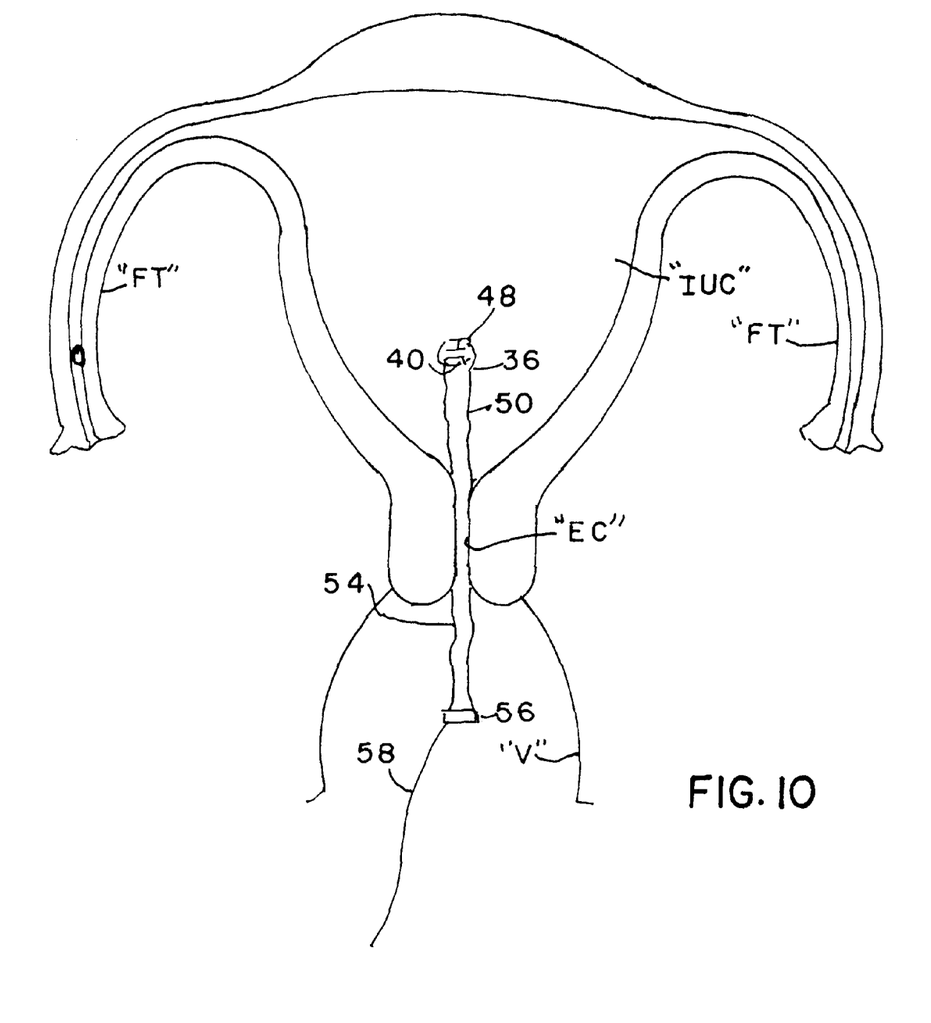
FIG. 10 is a representation of the uterine cavity, with the reservoir balloon and the retention balloon fully discharged, and just prior to removal from the uterine cavity.

The retention balloon 50 and the reservoir balloon 6 are maintained within the intrauterine cavity "IUC" over an extended period of time, as represented by FIGS. 8 and 9. During the first twenty-four hours of emplacement of the insertion apparatus within the intrauterine cavity "IUC", a continuous supply of treatment medium or capacitated sperm 30 is supplied through the release valve 48 and into the uterus "IUC" and fallopian tubes "FT". During the next twenty-four to forty eight hours of emplacement of the insertion apparatus within the intrauterine cavity "IUC", the reservoir balloon 36 becomes substantially deflated, and has discharged its volume of treatment medium or spermatozoa, as is represented by FIG. 10. This total elapsed time of about forty-eight to about sixty hours is sufficient to provide a medicament treatment or a continuum of capacitated sperm 30 to the fallopian tubes "FT" and ovum, to ensure fertilization in a most nearly natural manner. Diminishment of volume of the reservoir balloon 36 is accompanied by a corresponding volumetric diminishment of the outer retention balloon 50.

After about sixty hours post-insertion of the insertion apparatus 20, the draw or pull-string 58 attached to the proximalmost end of the elongated neck 54, may be pulled so as to release the seal valve 56 thereat. The outer retention balloon 50 is thereby completely deflated, as represented in FIG. 10, and the entire remaining reservoir balloon 36 and retention balloon 50 may be removed from the intrauterine cavity "IUC" through the endocervical canal "EC", and may be discarded. This procedure permits removal of this device without necessitating a return visit to a physician's office.

Thus, treatment of a female, human or animal, may be accomplished for insemination or treatment by a medicament, through a process which closely corresponds to a natural insemination, for an extended period of time such being the most likely to cause proper fertilization.

I claim:

1. A method for the application of a treatment medium to the intrauterine cavity of a female, comprising the steps of:
   introducing a first pressurizable chamber within a intrauterine cavity of a female;
   introducing a second pressurizable chamber radially outwardly of said first pressurizable chamber;
   filling said first pressurizable chamber with a treatment medium; and
   filling said outer pressurizable chamber with a pressurizable fluid, so as to effect discharge of said treatment medium from said innermost first pressurizable chamber over an extended period of time.

2. The method as recited in claim 1 including the step of introducing said treatment medium into said first pressurizable chamber through an elongated catheter.

3. The method as recited in claim 2, including the step of introducing a pressurizable medium into said outer-chamber through said elongated catheter.

4. The method as recited in claim 3, including the step of:
   removing said catheter from said pressurizable chambers.

5. The method as recited in claim 4, wherein said treatment medium comprises a charge of spermatozoa.

6. A method for the prevention of exposure of spermatozoa to an intrauterine environment during passage through the cervical canal, comprising the steps of:
   placing a first reservoir balloon on a distal end of an elongated hollow catheter shaft;
   placing a second reservoir balloon readily outwardly of said first balloon about said distal end of the elongated shaft;
   arranging a slow-release valve on a distal end of said reservoir balloon to permit slow-release of spermatozoa from said reservoir balloon;
   inserting said first and second balloons through the end of a cervical canal and into a uterine cavity; and
   arranging a pre-loaded syringe of spermatozoa in communication with said elongated catheter, to per the introduction of said spermatozoa through said elongated catheter and into said reservoir balloon, for subsequent time release expulsion through said discharge valve and into the uterine cavity.

7. The method as recited in claim 6, including the step of:
   arranging an airtight seal between said first reservoir balloon and a seal between said second balloon and said elongated catheter shaft, so as to prevent leakage of air therebetween.

8. The method as recited in claim 6, including the step of:
   placing a valve at said seal at the proximalmost end of the said first reservoir balloon, so as to permit said valve to seal said first reservoir balloon upon withdrawal of the catheter therethrough.

9. An apparatus for the introduction of a treatment medium into the uterine cavity of a female reproduction system, comprising:

an elongated, hollow, flexible catheter shaft having a proximal end and a distal end;

a first chamber arranged on said distal end of said catheter;

a second chamber arranged about said first chamber, said first and second chambers arranged for introduction into a female uterus, said first chamber being responsive to said second chamber to release a treatment medium in the uterus.

10. The apparatus as recited in claim 9, including:

a release valve arranged on a distal end of said first chamber to permit said first chamber to release said treatment medium into the uterus in a slow manner upon said second chamber having a pressurized effect on said first chamber.

11. The apparatus as recited in claim 10, including:

an air tight seal arranged on a proximal end of said first chamber to slidingly mate about said catheter shaft in a sealed manner.

12. The apparatus as recited in claim 11, including:

a syringe-receiving coupling arranged on said proximal end of said catheter shaft to permit the introduction of said treatment medium into said catheter and into one of said chambers.

13. The apparatus as recited in claim 12, including:

a withdrawal mechanism attached to said proximal end of said second chamber to permit the easy withdrawal of said first and second chambers from a uterine cavity upon complete release of treatment medium therefrom.

14. The apparatus as recited in claim 13, wherein said treatment medium comprises a charge of spermatozoa.

15. The apparatus as recited in claim 13, wherein said first and second chambers are comprised of flexible, collapsible, radially expandable, pressurizable balloons.

16. The apparatus as recited in claim 15, wherein said second chamber is pressurized by introduction of air therein, and said first chamber is pressurized by the introduction of treatment medium therein.

17. The apparatus as recited in claim 16, wherein said second chamber pressurizes said first chamber radially inwardly to effect release of said treatment medium therefrom.

18. The apparatus as recited in claim 17, wherein said second chamber is arranged to be pressurized radially inwardly by the disposition of said second chamber within a uterine cavity.

19. The apparatus as recited in claim 13, wherein said second chamber has a proximal end, with a valve in said proximal end thereof, which valve is removable therefrom, by a user of said apparatus.

20. The apparatus as recited in claim 13, wherein said withdrawal mechanism comprises an elongated neck of said second chamber which may be retracted from the uterine cavity in which said second chamber was placed, upon completion of a discharge of any contents of said first and second chambers.

21. The method of introduction of a treatment device into the lower uterine segment and endocervix, to contain sperm during transcervical intrauterine insemination, comprising the steps of:

inserting a pair of radially adjacent inner and outer expandable balloons on an end of an elongated catheter, into the intrauterine cavity of the female reproductive system;

injecting a treatment medium through said elongated catheter and into an inner balloon of said balloons;

pressurizing said outer balloon with a pressurized medium through said elongated catheter; and removing said elongated catheter from said inner and outer balloons so as to permit intrauterine wall pressure against said outer balloon and time-released discharge of said treatment medium through a slow release valve in said inner balloon.

\* \* \* \* \*